United States Patent [19]
Takebe et al.

[11] Patent Number: 5,885,632
[45] Date of Patent: *Mar. 23, 1999

[54] PROCESS FOR PREPARING A PRODUCT FROM A PULSE CROP AS A STARTING MATERIAL AND A FOOD CONTAINING THE PRODUCT PREPARED FROM A PULSE CROP AS A STARTING MATERIAL

[75] Inventors: Minoru Takebe; Yoshio Ando, both of Tokyo; Sunao Kikushima, Kyoto, all of Japan

[73] Assignee: Nichimo Co., Ltd., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 492,126

[22] PCT Filed: Dec. 12, 1994

[86] PCT No.: PCT/JP94/02103

§ 371 Date: Sep. 8, 1995

§ 102(e) Date: Sep. 8, 1995

[87] PCT Pub. No.: WO95/16362

PCT Pub. Date: Jun. 22, 1995

[30]  Foreign Application Priority Data

Dec. 14, 1993  [JP]  Japan ..................................... 5-313254

[51] Int. Cl.⁶ ....................................................... A23L 1/20
[52] U.S. Cl. ............................................................ 426/46
[58] Field of Search .................................................. 426/46

[56]  References Cited

U.S. PATENT DOCUMENTS 4,366,248  12/1982  Zilliken ..................................... 435/125
5,316,770   5/1994  Edwards, Jr. .
5,352,384  10/1994  Shen .

FOREIGN PATENT DOCUMENTS 0 649 600 A1   4/1995  European Pat. Off. .
WO93 23069    11/1993  WIPO .

OTHER PUBLICATIONS

Journal of Industrial Microbiology, 2 (1987) 195–200 published in 1987.

Journal of Agricultural and Food Chemistry, vol. 41, No. 11, Nov. 1993, Washington, U.S.

"Genistein, Daindzein and Their Beta–Glycoside Conjugates: Antitumor Isoflavones in Soybean Foods from American and Asian Diets" L. Coward, et al.

Database Chemabs, Chemical Abstracts Service, Columbus Ohio, U.S.; AN 115: 134519, 1990, XP00202860, "abstract" & Nippon Shokuhin Kogyo Gakkaishi, vol. 37, No. 10, JP. pp. 786–92.

Journal of the Science of Food and Agriculture, vol. 28, 1977, Barking GB, pp. 381–383, XP002028061, S. Sudarmadji: "The Phytate and Phytase of Soybean Tempeh".

A. Smit: "Soybeans: Chemistry and Technology", 1972, AVI, USA, XP002028059, pp. 389–397, p. 394–p. 397.

Sutardi et al., "Reduction in phytic acid levels in soybeans during tempeh production, storage, and frying", Journal of Food Science, 50:260–263., Jan. 1985.

Primary Examiner—Marian C. Knode
Assistant Examiner—Brenda G. Brumback
Attorney, Agent, or Firm—Koda & Androlia

[57]  ABSTRACT

A process for preparing a product from a pulse crop as a starting material and a food containing the product prepared from a pulse crop as a starting material are disclosed according to the present invention, thereby enabling a food, a livestock feed, an aquacultural feed or the like to be efficiently prepared, which is made from a leguminous crop or a defatted product thereof or the like, which has excellent carcinopreventive and carcinostatic activities, osteoprosis therapeutic effect and immunosuppressive effect, and which can be ingested in a sufficient amount, and thereby enabling a wholesome food such as a biscuit having the above-mentioned excellent pharmacological activities. Any conventional product made from a pulse crop does not have such excellent pharmacological activities and a process for preparing the same is poor in efficiency. Significant characteristic feature of the present invention resides in that glycosidic saccharides are hydrolytically separated from isoflavone compounds contained in a pulse crop to form isoflavone compounds containing aglycones in a large amount and that phytic acid contained in a pulse crop is removed to obtain a product having excellent pharmacological activities.

10 Claims, 2 Drawing Sheets

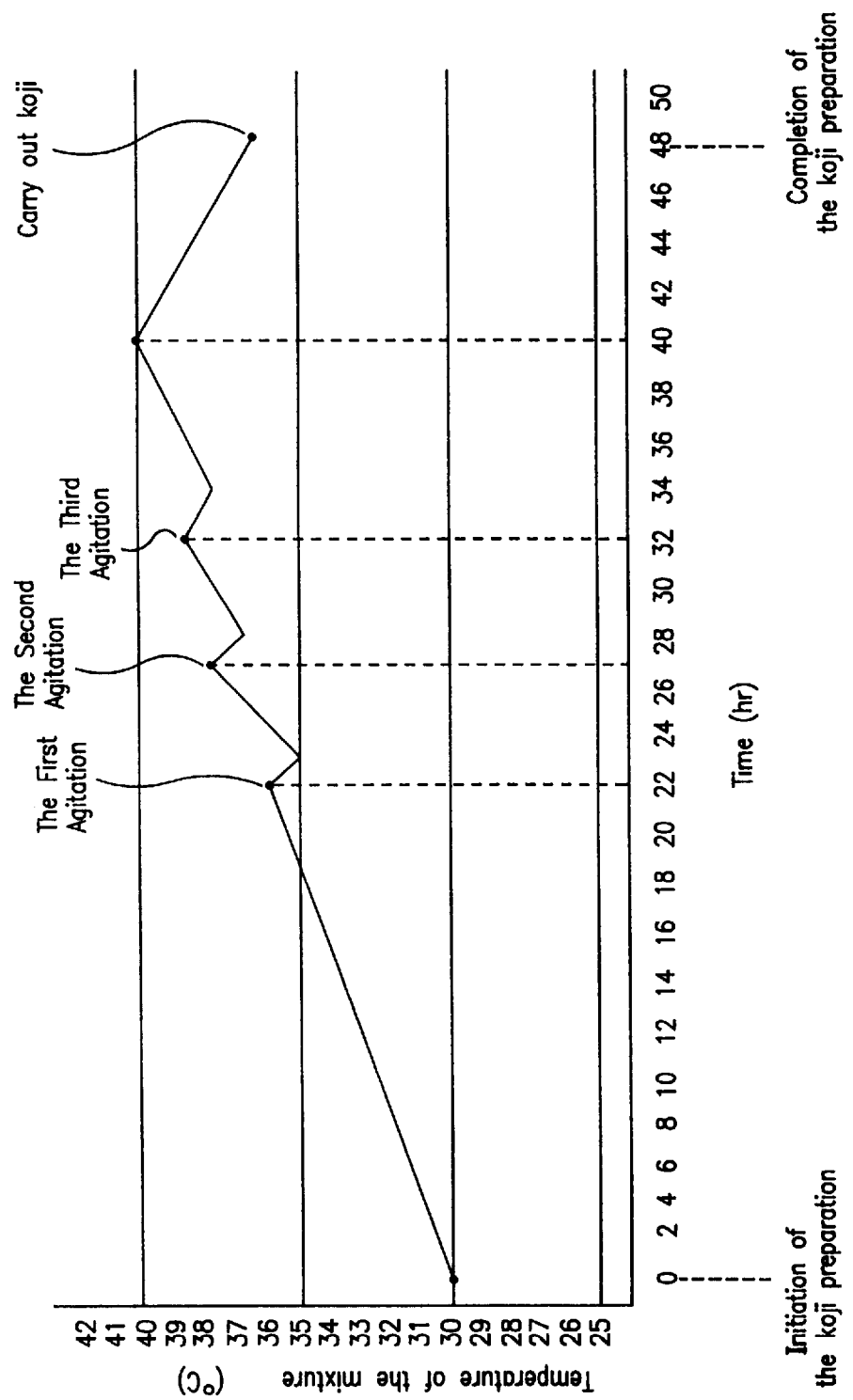

PROCESS FOR PREPARING A PRODUCT FROM A PULSE CROP AS A STARTING MATERIAL AND A FOOD CONTAINING THE PRODUCT PREPARED FROM A PULSE CROP AS A STARTING MATERIAL

This application is based upon the International Application PCT/JP94/02103, the International Publication Number WO95/16362 published on Jun. 22, 1995.

TECHNICAL FIELD

The present invention relates to a process for preparing a product from a pulse crop as a starting material and a food containing the product prepared from a pulse crop as a starting material.

In the present invention, the term "pulse crop" means leguminous crops such as soybean, defatted products thereof and the like, and the term "product made from a pulse crop as a starting material" means foods, livestock feeds, aquacultural feeds and the like which are made from the above-mentioned pulse crop.

BACKGROUND ART

In general, soybean which is one of the pulse crops contains isoflavone compounds including daidzin, daidzein, genistin and genistein.

The isoflavone compounds are represented by the following formula and Denotative Table.

| Denotative Table | | |
|---|---|---|
| | R1 | R2 |
| daidzin | H | glucose |
| daidzein | H | H |
| genistin | OH | glucose |
| genistein | OH | H |

Of these isoflavone compounds, daidzein is an aglycone of daidzin having its glucose as a glycosidic saccharide hydrolytically separated therefrom, and genistein is an aglycone of genistin having its glucose as a glycosidic saccharide hydrolytically separated therefrom. With respect to the isoflavone compounds, contents thereof and percentages between daidzin and daidzein and between genistin and genistein in a defatted soybean are as shown in the following Table 1.

TABLE 1

| | daidzin | daidzein | genistin | genistein |
|---|---|---|---|---|
| defatted soybean | 100 (96.9%) | 3.2 (3.1%) | 180 (97.7%) | 4.2 (2.3%) |

(unit: mg/100g)

It is understood from Table 1 that, in soybean, daidzin and genistin are contained in larger amounts while daidzein and genistein which are aglycones thereof are contained in smaller amounts.

On the other hand, it has been reported that a glycosidic saccharide is hydrolyzed from an isoflavone compound contained in soybean to form an aglycone in the course of soy sauce or miso (fermented soybean paste) preparation [see Sho-Ken (Soy-research) by Kiyoshi Kihara, vol.16, No.5, page 190 (1990)].

According to this report, however, although hydrolysis of a glycosidic saccharide proceeds to some extent by cooking of a defatted soybean or in a koji preparation step, most of the saccharide has already hydrolytically been separated in soy sauce sediment or soybean miso. Accordingly, it is difficult to employ these for a process for preparing a product from a pulse crop as a starting material.

Further, many reports have been made on pharmacological activities of aglycones derived from hydrolysis of glycosidic saccharides from isoflavone compounds.

For example, genistein has been ascertained to be a tyrosine kinase inhibitor (TK inhibitor). Since tyrosine kinase is essentially responsible for cancer-induction by an onocogene, carcinostatic activities of genistein as a TK inhibitor are confirmed and the effect thereof has drawn attention [Akiyama et al.: Biochemistry, vol.59, No.9, page 1016 (1987)].

Further, estrogenic activities of an isoflavone compound have also attracted attention and have been confirmed to have osteoprosis therapeutic effect and immunosuppressive effect. In particular, genistein which is an aglycone of an isoflavone compound has notable estrogenic activities, and this activities enable osteopenia (bone resorption) to be suppressed.

Accordingly, many proposals concerning isoflavone compounds contained in soybean have been made in Japanese Unexamined Patent Publication No.126,186/1987, Japanese Unexamined Patent Publication No.258,669/1989, Japanese Unexamined Patent Publication No.170,756/1993, and so on.

DISCLOSURE OF INVENTION

According to the method described in Japanese Unexamined Patent Publication No.126,186/1987, however, most of the resulting isoflavone compounds are daidzin and genistin which each have a glycosidic saccharide, and aglycones are contained in the resultant in small amounts. Thus, it is impossible to obtain foods and the like which have excellent pharmacological effect as mentioned above.

The method described in Japanese Unexamined Patent Publication No.258,669/1989 is one which comprises hydrolytically separating a glycosidic saccharide from an isoflavone compound by action of β-glucosidase which is one of enzymes contained in soybean per se. However, aglycones are formed in a small proportion.

The method described in Japanese Unexamined Patent Publication No.170,756/1993 is one which comprises extractively separating isoflavone compounds from aglycones of isoflavones formed in a soy sauce sediment or soy sauce. Although aglycones of isoflavones are formed in the course of soy sauce preparation and yet formed in a very high proportion as described above, there is the following disadvantage. That is, aglycones of isoflavones are present in soy sauce sediment because of their insolubility and soy sauce sediment per se does not serve as a food, and hence the method cannot be employed as a method for preparing a food. Further, aglycones of isoflavones are also formed in a soybean miso at initial stage of preparation. However, a soybean miso has a problem that it should be avoided to ingest a soybean miso in a large amount because it is a highly salinized food.

Although ingestion of foods in a satisfactory amount which contain a sufficient amount of such isoflavone aglycones having excellent pharmacological activities as mentioned above enables dietarily desired life to be realized which exhibits excellent effect in terms of health maintenance of a human being, no food has heretofore satisfied this expectation.

Thus, the advent of foods which have excellent carcinopreventive and carcinostatic activities, osteoprosis therapeutic activities, and immunosuppressive activities, and which can be ingested in a satisfactory amount.

With respect to osteoprosis, it is desired to remove phytic acid, which inhibits calcium from being absorbed in a body, from a pulse crop.

In soybean which is one of beans, phytic acid is contained in an amount of about 1 to 2% by weight. Phytic acid is residually present also in a product made from soybean and inhibits activities of a vitamin B complex contained in the product to prevent absorption of minerals and the like contained in the product. Further explanatively, phytic acid is a compound having such a structure that myo-inositol has its all hydroxyl groups each bonded with a phosphoric acid group, and chelates with a nutritionally important trace metal element to form hardly soluble compound. Accordingly, when a food with high phytic acid content is ingested by a human being or animal, normal intestinal absorption of such metals, for example, calcium, magnesium, iron, zinc and the like is prevented to cause various deficiencies. It has further been found that phytic acid present in a product including a soy protein isolate prevents a monogasteric animal from utilizing zinc in a food. Further, phytic acid is known to have inhibitory activities on various digestive enzymes in a gastrointestinal digestive tract on which ions of minerals such as calcium act as activators and which include α-amylase, pepsin and trypsin. It is, therefore, desired to remove phytic acid from the product.

Heretofore, however, it has been impossible to remove phytic acid successfully.

The present invention has been made in view of these points. It is, therefore, an object of the present invention to provide a process for preparing a product from a pulse crop such as a food, a livestock feed, an aquacultural feed or the like, which is made from a pulse crop, which has excellent carcinopreventive and carcinostatic activities, osteoprosis therapeutic effect and immunosuppressive effect, and which can be ingested in a sufficient amount.

It is another object of the present invention to provide a healthful food, such as a biscuit or the like which contains a product that is made from a pulse crop and that has properties excellent in carcinopreventive and carcinostatic activities, osteoprosis therapeutic effect and immunosuppressive effect.

To attain the above object, the process of the present invention for preparing a product from a pulse crop as a starting material comprises:

inoculating a koji starter on a pulse crop to prepare koji; and adding water to the resultant from the koji preparation treatment to advance hydrolysis of a protein contained in the resultant;

wherein in the course of the koji preparation and the proteolysis, separation of glycosidic saccharides from isoflavone compounds contained in the pulse crop is advanced to form isoflavone compounds containing aglycones in a large amount, thereby obtaining a product from the pulse crop as a starting material.

Further, the process of the present invention for preparing a product from a pulse crop as a starting material comprises:

inoculating a koji starter on a pulse crop to prepare koji; and adding water to the resultant from the koji preparation treatment to advance hydrolysis of a protein contained in the resultant;

wherein in the course of the koji preparation and the proteolysis, removal of phytic acid is advanced in parallel with the separation of glycosidic saccharides from isoflavone compounds contained in the pulse crop to form isoflavone compounds containing aglycones in a large amount, thereby obtaining a product from the pulse crop as a starting material.

Still further, the food of the present invention containing a product prepared from a pulse crop as a starting material contains a product prepared from a pulse crop as a starting material by steps of:

inoculating a koji starter on a pulse crop to prepare koji; and adding water to the resultant from the koji preparation treatment to advance hydrolysis of a protein contained in the resultant;

wherein in the course of the koji preparation and the proteolysis, separation of glycosidic saccharides from isoflavone compounds contained in the pulse crop is advanced to form isoflavone compounds containing aglycones in a large amount, thereby obtaining a product from the pulse crop as a starting material.

Further, the food of the present invention containing a product prepared from a pulse crop as a starting material contains a product prepared from a pulse crop as a starting material by steps of:

inoculating a koji starter on a pulse crop to prepare koji; and adding water to the resultant from the koji preparation treatment to advance hydrolysis of a protein contained in the resultant;

wherein in the course of the koji preparation and the proteolysis, removal of phytic acid is advanced in parallel with the separation of glycosidic saccharides from isoflavone compounds contained in the pulse crop to form isoflavone compounds containing aglycones in a large amount, thereby obtaining a product from the pulse crop as a starting material.

The present invention is constructed as described above and hence exhibits the following extremely excellent effects.

According to the process of the present invention for preparing a product from a pulse crop as a starting material it is realized that koji mold is propagated in koji preparation by inoculating koji starter on a pulse crop to hydrolytically separate glycosidic saccharides from isoflavone compounds contained in the pulse crop, and hydrolysis of a protein contained in the resultant from the koji preparation treatment is advanced by adding water thereto in parallel with further hydrolytic separation of glycosidic saccharides from isoflavone compounds contained in the pulse crop to form isoflavone compounds containing aglycones in a large amount.

According to the process of the present invention for preparing a product from a pulse crop as a starting material it is realized that koji mold is propagated in koji preparation by inoculating koji starter on a pulse crop to hydrolytically separate glycosidic saccharides from isoflavone compounds contained in the pulse crop and concurrently therewith to remove phytic acid in the pulse crop, and hydrolysis of a protein contained in the resultant from the koji preparation treatment is advanced by adding water thereto in parallel with further hydrolytic separation of glycosidic saccharides from isoflavone compounds contained in the pulse crop to form isoflavone compounds containing aglycones in a large amount and in parallel with further removal of phytic acid.

The koji mold as mentioned above produces various enzymes, and of these enzymes, β-glucosidase, phytase, phosphatase and protease are utilized to hydrolytically separate glycosidic saccharides from isoflavone compounds and to remove phytic acid contained in a pulse crop.

The food of the present invention containing a product made from a pulse crop is a food containing the above-mentioned product made from a pulse crop. The food contains the product having excellent carcinopreventive and carcinostatic activities, osteoprosis therapeutic effect, immunosuppressive effect and the like, and accordingly, it is capable of maintaining parson's health constantly good when ingested as a health food.

The present invention is constructed and functions as described above, and hence the product prepared in accordance therewith is derived from a pulse crop and is of excellence in carcinopreventive and carcinostatic activities, osteoprosis therapeutic effect, immunosuppressive effect and the like. Further, the product is easy of digestion and yet easy of absorption because it is prepared through proteolysis. Accordingly, the product is nutritionally excellent in terms of protein utilization efficiency. In addition, the product can be used for a food, a livestock feed, an aquacultural feed and the like which may be ingested in a satisfactory amount, because no common salt has been added thereto.

Further, a food such as a biscuit which is so prepared as to contain the above-mentioned product is one having excellent carcinopreventive and carcinostatic activities, osteoprosis therapeutic effect, immunosuppressive effect and the like, and accordingly, it is capable of maintaining parson's health constantly good when ingested as a health food. In particular, genistein in isoflavone compounds containing aglycones in a large amount obtained by hydrolytically separating glycosidic saccharides from isoflavone compounds is highly effective because of its high carcinopreventive and carcinostatic activities on mastocarcinoma, prostatitic cancer and the like.

BRIEF DESCRIPTION OF THE DRAWINGS

FIG. 2 is a diagram showing temperature characteristics of a mixture with progress of koji preparation time.

BEST MODE FOR CARRYING OUT THE INVENTION

Figure 1:
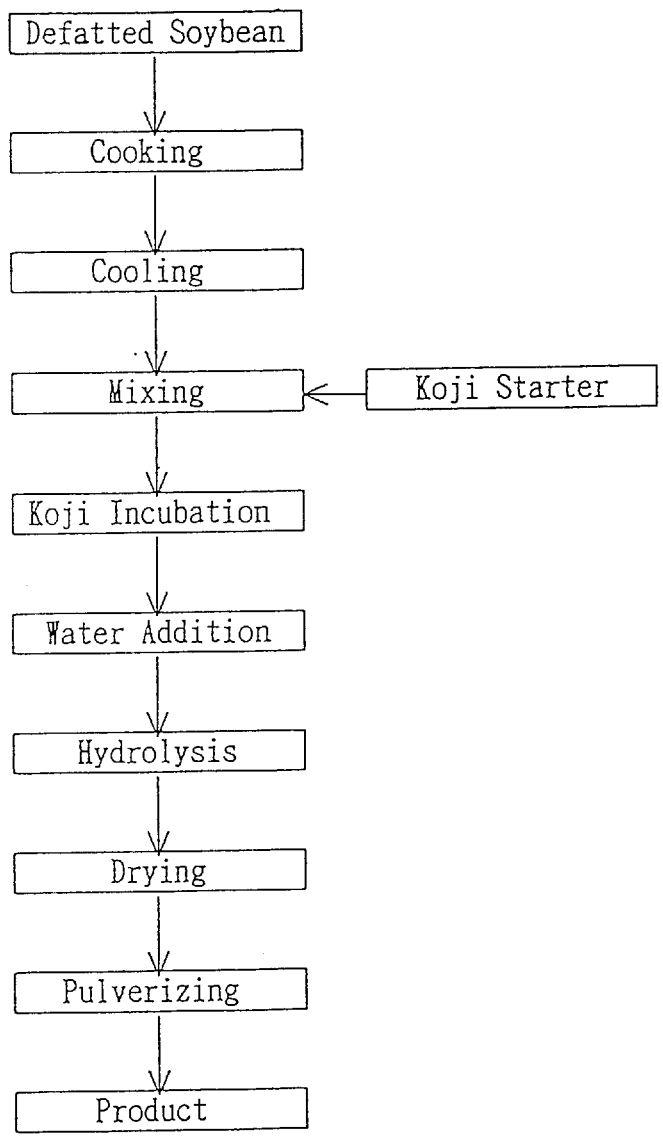
FIG. 1 is a flow chart showing one mode of the process for preparing a product from a pulse crop according to the present invention, which comprises forming aglycones having high pharmacological activities from isoflavone compounds contained in a defatted soybean, and one mode of the process which further comprises concurrently removing phytic acid contained in the defatted soybean.

Now, embodiments of the present invention will be described with reference to FIG. 1.

FIG. 1 is a flow chart showing one mode of the process for preparing a product from a pulse crop according to the present invention, which comprises hydrolytically separating glycosidic saccharides from isoflavone compounds contained in a defatted product of soybean which is one of pulse crops to form isoflavone compounds containing aglycones in a large amount in the resulting product, and one mode of the process which further comprises concurrently removing phytic acid contained in the defatted soybean.

In the first place, the process for preparing a product will be described, which comprises forming isoflavone compounds containing aglycones in a large amount.

Explanation will be given along the procedure in FIG. 1. First, a defatted soybean is cooked. By effecting the cooking, propagation of koji is facilitated. The cooking of the defatted soybean may be conducted batchwise or continuously according to the purpose of preparation or the like.

After completion of the cooking, the defatted soybean is once cooled to adjust water content in the defatted soybean to a level allowing koji to propagate (for example, 40% by weight).

Incidentally, when a defatted soybean or the like is used as a starting material, the step of cooking may be omitted.

The defatted soybean thus adjusted in the water content is subjected to the process of the present invention as follows.

That is, the defatted soybean already cooked is inoculated with a koji starter of a koji mold at a predetermined weight ratio, and mixing is conducted to uniformness.

Then, the mixture is charged into a device for preparing koji and kept in a heated condition at an initial temperature of about 28° to 30° C. for a predetermined period of time to ferment the defatted soybean having a water content as low as 40% by weight with koji, thereby hydrolytically separating glycosidic saccharides from isoflavone compounds contained in the defatted soybean to form aglycones. The koji preparation is continued until an enzyme necessary for hydrolytically separating the glycosidic saccharides from the isoflavone compounds.

In this stage, the koji is propagated on the defatted soybean to produce β-glucosidase which is an enzyme hydrolytically separating a glycosidic saccharide from an isoflavone compound, and by this enzyme, glycosidic saccharides are hydrolytically separated from the isoflavone compounds contained in the defatted soybean to form aglycones of the isoflavones.

As the koji starter for the koji preparation, there may be used those which are used preparation of Japanese traditional fermented foods and tempeh and which are safely used for foods, for example, those classified as Aspergillus genus such as *Aspergillus usamii, Aspergillus kawachi, Aspergillus awamori, Aspergillus saitoi, Aspergillus oryzae* and *Aspergillus niger*; and those classified as Rhizopus genus.

The fermentation time depends upon the type of koji mold used. However, it is at least 24 hours and is appropriately selected to be sufficient one for hydrolytically separating glycosidic saccharides from the isoflavone compounds contained in the defatted soybean to satisfactory extent.

The temperature of the mixture in the device for preparing koji changes with time, for example, as shown in FIG. 2, as koji preparation proceeds. That is, the temperature gradually rises until the state of the first agitation (mori) is reached 22 hours after the initiation of the koji preparation, and the temperature slightly falls past the first agitation. Then, the temperature rises again until the stage of the second agitation (Naka) is reached 27 hours after the initiation of the koji preparation. Upon stirring the mixture at the "intermediary", the temperature slightly falls. Then, the temperature rises again until the stage of the third agitation (Shimai) is reached 32 hours after the initiation of the koji preparation. Upon stirring the mixture at the the third agitation (Shimai), the temperature slightly falls. Then, the temperature rises again up to 40 hours after the initiation of the koji preparation. Thereafter, the temperature gradually falls until the koji preparation reaches completion 48 hours after the initiation of the koji preparation.

Then, water is added to the product resulting from the koji preparation, and the mixture is kept in a heated condition at 30° to 65° C. for a predetermined period of time to hydrolyze protein while sufficiently separating glycosidic saccharides from the isoflavone compounds contained in the defatted soybean by the action of β-glucosidase contained in the product to form aglycones of isoflavones.

With respect to the hydrolysis of the protein, hydrolysis time and hydrolysis temperature are appropriately selected depending upon the type of koji used so that glycosidic saccharides are separated from the isoflavone compounds contained in the defatted soybean to satisfactory extent.

In this manner, organic acids are formed in the initial stage of the fermentation to inhibit contaminants in the defatted soybean from propagating, thereby eliminating undesired possibility of secondary contamination. Consequently, a product made from a defatted soybean as a starting material can be mass-produced. Further, even if the water content is not low, it is possible to carry out such treatment for separating glycosidic saccharides from the isoflavone compounds sufficiently.

Table 2 shows contents of isoflavone compounds in 100 g of a defatted soybean which is prepared by subjecting an untreated defatted soybean to koji preparation initiated at an initial temperature of 30° C. and completed over a period of 48 hours, adding water to the resulting product in the same weight as that of the resulting product, and subjecting the mixture to hydrolysis of proteins at 30° C. for 24 hours.

TABLE 2

| daidzin | daidzein | genistin | genistein |
|---------|----------|----------|-----------|
| 25      | 74       | 53       | 59        |

(unit: mg/100g)

According to Table 2, daidzein and genistein which are aglycones of isoflavone compounds are contained in greatly increased amounts of 74 mg and 59 mg which are about 23 times and 14 times as large as the amounts thereof in the conventional example shown in Table 1, respectively. From this, it is understood that daidzein and genistein can be formed in further increased amounts by effecting the hydrolysis of proteins for 24 hours or more after the completion of the koji preparation.

In another Example, the treatment according to the process of the present invention was applied to an untreated defatted soybean and a soy protein isolate, and Table 3 comparatively shows, for the same purpose as that of Table 2, measurements thereon prior and posterior to the treatment.

Explanation is first made with respect to one of them, the defatted soybean. Proportions of starting materials and koji starter was such that 100 g of a defatted soybean, 0.1 g of a roughly polished rice, and 8×10$^7$ koji spores/g were used. With such proportions, the untreated defatted soybean was subjected to koji preparation initiated at an initial temperature of 30° C. and completed over a period of 48 hours, and water was added to the resulting product in the same weight as that of the resulting product, and the mixture was subjected to hydrolysis of proteins at 50° C. for 48 hours. The results are as shown in Table 3.

As the other of them, i.e., the commercially available soy protein isolate, Fujinic 200 (trade name) manufactured by Fuji-Purina k.K. was used. Proportions of starting materials and koji starter was such that 100 g of the commercially available soy protein, 0.1 g of a roughly polished rice, and 8×10$^7$ koji spores/g were used. With such proportions, the untreated commercially available soybean protein was subjected to koji preparation initiated at an initial temperature of 30° C. and completed over a period of 48 hours, and water was added to the resulting product in the same weight as that of the resulting product, and the mixture was subjected to hydrolysis of proteins at 50° C. for 48 hours. The results are as shown in Table 3.

TABLE 3

|           | defatted soybean | | commercially available soybean protein | |
|-----------|------|--------------|------|------|
|           | pre  | post         | pre  | post |
| daizin    | 100  | not detected | 90   | 1.0  |
| daizein   | 3.2  | 70           | 5.3  | 100  |
| genistin  | 120  | 1.3          | 120  | 3.3  |
| genistein | 4.2  | 64           | 4.4  | 94   |

(unit: mg/100g)

According to Table 3, in the defatted soybean, daidzein and genistein which are aglycones of isoflavone compounds are contained in greatly increased post-treatment amounts of 70 mg and 64 mg which are about 22 times and 15 times as large as the pre-treatment values, respectively. In addition, daidzin which is an isoflavone compound having a glycosidic saccharide is decomposed to an undetectable extent, and the amount of genistin is extremely reduced to a level as low as 1.3 mg.

Likewise, in the commercially available soybean protein, daidzein and genistein which are aglycones of isoflavone compounds are contained in greatly increased post-treatment amounts of 100 mg and 94 mg which are about 19 times and 21 times as large as the pre-treatment values, respectively. In addition, the amounts of daidzin and genistin which are isoflavone compounds each having a glycosidic saccharide are extremely reduced to a level as low as 1.0 mg and 3.3 mg, respectively.

As described above, according to the present invention, of isoflavone compounds contained in soybean, aglycones having high pharmacological activities can be prepared at extremely high formation ratios.

In the next place, the process for preparing a product will be described which comprises forming isoflavone compounds containing aglycones in a large amount, and concurrently removing phytic acid contained in a defatted soybean.

The preparation procedure of the invention is conducted in substantially the same manner as in the previously described preparation procedure. However, in the koji preparation step, water addition step and hydrolysis step, phytic acid is removed from the defatted soybean in parallel with the formation of isoflavone compounds containing aglycones in a large amount.

Then, each of these steps will be described.

In the koji preparation step, a mixture of a defatted soybean and koji starter is charged into a device for preparing koji and kept in a heated condition at an initial temperature of about 28° to 30° C. for a predetermined period of time to ferment the defatted soybean having water content as low as 40% by weight by means of koji starter until phytic acid in the defatted soybean is sufficiently removed.

In this case, koji mold is propagated on the defatted soybean to produce phytase and phosphatase which are enzymes decomposing phytic acid, and by the enzymes, phytic acid in the defatted soybean is hydrolytically removed.

Specifically, from phytic acid which is a compound having such a structure that myo-inositol has all of its hydroxyl groups each bonded with a phosphoric acid group, the phytic acid-decomposing enzymes liberate the phosphoric acid group(s) to form inositol pentaphosphate, inositol tetraphosphate, inositol triphosphate, inositol diphosphate, inositol monophosphate or inositol alone or a mixture thereof, thereby removing phytic acid.

As the koji starter for the koji preparation, there may be used koji molds which are used preparation of Japanese traditional fermented foods and tempeh and which are safely used for foods, for example, those having high phytase and phosphatase potency and classified as Aspergillus genus such as *Aspergillus usamii, Aspergillus kawachi, Aspergillus awamori, Aspergillus saitoi, Aspergillus oryzae* and *Aspergillus niger*; and those having high phytase and phosphatase potency and classified as Rhizopus genus.

The fermentation time depends upon the type of koji mold used. However, it is at least 24 hours and is appropriately selected to be sufficient one for removing phytic acid contained in the defatted soybean to satisfactory extent.

In the subsequent water addition step and hydrolysis step, water is added to the product resulting from the koji preparation, and the mixture is kept in a heated condition at 30° to 55° C. for a predetermined period of time to hydrolyze protein while sufficiently reducing the amount of phytic acid contained in the defatted soybean by the hydrolytic action of phytase, phosphatase and/or protease contained in the product.

With respect to the hydrolysis of protein, hydrolysis time and hydrolysis temperature are appropriately selected depending upon the type of koji used so that phytic acid contained in the defatted soybean is sufficiently removed.

The removal of phytic acid is effected by liberating at least one phosphoric acid group from phytic acid which is inositol hexaphosphate. In this connection, however, at least two phosphoric acid groups-liberated resultants, i.e., inositol tetraphosphate, inositol triphosphate, inositol diphosphate, inositol monophosphate and inositol are water-soluble and have activities to greatly facilitate absorption of a mineral such as calcium contained in a product made from a cereal.

Further descriptively, the above-mentioned inositol hexaphosphate and inositol pentaphosphate have strong ion capturing activities and prevent captured calcium ion from being liberated, thereby strongly inhibit absorption of calcium. On the other hand, inositol tetraphosphate to inositol monophosphate have such preferable affinities that they preferably capture calcium but readily liberate captured calcium on occasion, thereby exhibiting characteristic activities to facilitate absorption of calcium.

It is, therefore, preferred to effect removal of phytic acid by liberating at least two phosphoric acid groups from phytic acid which is inositol hexaphosphate to form inositol tetraphosphate, inositol triphosphate, inositol diphosphate, inositol monophosphate or inositol alone or a mixture thereof, thereby obtaining a product which enables minerals to be absorbed efficiently. In this case, it is preferred to control the number of the phosphoric acid groups liberated from phytic acid by adjusting the fermentation time, and hydrolysis time and hydrolysis temperature depending upon the type, state, properties and amount of the pulse crop, the type, state, properties and amount of the koji, and type and properties of the intended product.

Table 4 shows phytic acid content in 100 g of a defatted soybean, with respect to an untreated defatted soybean; defatted soybeans A and B which are prepared using two different shochu kojis (*Aspergillus niger* and *Aspergillus awamori*) and each prepared by subjecting a defatted soybean to koji preparation initiated at an initial temperature 30° C. and completed over a period of 48 hours, adding water to the resulting product in the same weight as that of the resulting product, and subjecting the mixture to hydrolysis of protein at 30° C. for 24 hours; and a defatted soybean subjected to conventional washing treatment with an alcohol.

TABLE 4

| defatted soybean | phytic acid content (mg/100g) |
|---|---|
| untreated defatted soybean | 999 (mg/100g) |
| shochu koji-treated d. s. A | not detected |
| shochu koji-treated d. s. B | not detected |
| alcohol-washed d. s. | 1,150 (mg/100g) |

(detection limit: 5mg/100g)

According to Table 4, in contrast to the phytic acid content of 999 mg (about 1%) in the untreated defatted soybean, no substantial phytic acid contents in the defatted soybeans A and B are detected, which are each prepared according to the present invention by subjecting an defatted soybean to shochu koji treatment, adding water to the resulting product in the same weight as that of the resulting product, and subjecting the mixture to hydrolysis of proteins at 30° C. for 24 hours. In other words, almost all phytic acid is decomposed in each of the defatted soybeans A and B.

On the other hand, the phytic acid content in the defatted soybean subjected to the conventional washing treatment with an alcohol is 1,150 mg and no reduction of the phytic acid content is observed.

As described above, according to the present invention, of isoflavone compounds contained in soybean, aglycones having high pharmacological activities can be prepared at extremely high formation ratios, and at the same time, phytic acid content in soybean can be greatly or almost completely reduced.

Next, a food containing the product made from a pulse crop according to the present invention will be described.

The food containing the product made from a pulse crop according to the present invention includes a food consisting only of the product made from a pulse crop which is prepared in accordance with the process of the present invention and a food containing the product in part.

The product made from a pulse crop as a starting material which is prepared in accordance with the process of the present invention is a food having an extremely low salinity, because it is prepared without being salified with common salt. Accordingly, the product can be ingested in a sufficient amount when served as a food. And yet, the food contains aglycones of isoflavones in a large amount, which exhibit excellent carcinopreventive and carcinostatic activities, osteoprosis therapeutic effect and immunosuppressive effect, thereby enabling dietarily desired life to be realized which exhibits excellent effect in terms of health maintenance of a human being.

For example, when the food containing the product made from a pulse crop according to the present invention is formed into a form convenient for eating such as a biscuit, cookie or the like, it is possible to ingest aglycones of isoflavones which have excellent carcinopreventive and carcinostatic activities, osteoprosis therapeutic effect and immunosuppressive effect while such an article is eaten as a food. In particular, by simply eating such a biscuit or the like in an amount covering the intake of aglycones of isoflavones per day which is required to attain carcinopreventive and carcinostatic effect, osteoprosis therapeutic effect and immunosuppressive effect, the biscuit or the like contributes to prevention of outbreak of the disorders.

Of these aglycones of isoflavones, genistein is effective for prevention and carcinostasis at an initial stage of mastocarcinoma, prostatitic cancer and the like. Accordingly, ingestion of the food containing the product made from a pulse crop according to the present invention contributes to prevention of outbreak of these cancers, thereby enabling dietarily desired life in terms of health maintenance to be realized.

Further, with respect to osteoprosis, while aglycones of isoflavones exhibit osteopenia preventive effect, the removal of phytic acid enables a vitamin B complex having growth promoting activities and antiadipohepatic activities and the like to be maintained highly active and hence exhibits facilitative effect on absorption of calcium contained in the pulse crop. Moreover, these effects synergestically provide a food having extremely excellent osteoprosis therapeutic effect. In particular, such a food exhibits significant effect when used in dietotherapy for a person hormone-relatedly susceptible to osteoprosis.

When the defatted soybean prepared in accordance with the above-described procedure is utilized as a feed or the like, as shown in FIG. 1, the defatted soybean prepared as in the above-described embodiments is dried and then pulverized to obtain a product as a pulverized defatted soybean having high pharmacological activities, such as a material for a livestock feed, an aquacultural feed or the like.

According to the present invention, formation of aglycones of isoflavone compounds contained in a pulse crop, which have high pharmacological activities, at an extremely high formation ratio; removal of phytic acid in the pulse crop; and hydrolysis of proteins are effected by propagation of living koji. Therefore, the formation of aglycones and the removal of phytic acid can be attained even if the pulse crop is in solid state or fluid state, thereby enabling simplified preparation procedure and reduced preparation cost to be realized.

Further, the preparation process of the present invention can be carried out using a conventional device for preparing koji without any alteration, and hence a basic device for production is not required to be specially manufactured, thereby providing wide utility.

It is to be noted that the present invention is by no means restricted to the above-described embodiments and that various alterations and modifications can be made according to need.

We claim:

1. A process for preparing a product from a pulse crop as a starting material which comprises the ordered steps of:
    preparing a koji preparation by the steps comprising:
        cooking said pulse crop,
        cooling said cooked pulse crop,
        adding water into said pulse crop,
        mixing a koji starter into said pulse crop,
        incubating said pulse crop while stirring, and
    hydrolyzing said koji preparation by adding water, whereby phytic acid contained in said pulse crop is removed and glycosidic saccharides contained in said pulse crop are hydrolyzed, thereby forming isoflavone compounds containing aglycones.

2. A process according to claim 1, wherein said pulse crop is kept between 30°–40° C. during said step of preparing a koji preparation.

3. A process according to claim 1, wherein said glycosidic saccharides contained in said pulse crop are converted into aglycones.

4. A process according to claim 1, wherein said koji starter comprises *Aspergillus*.

5. A process according to claim 1, wherein said step of hydrolyzing said koji preparation comprises adding a quantity of water approximately equal in weight to the weight of said koji preparation.

6. A process for preparing a product in a bulk quantity from a pulse crop as a starting material which comprises the ordered steps of:
    preparing a koji preparation by the steps comprising:
        cooking said pulse crop,
        cooling said cooked pulse crop,
        adding water into said pulse crop,
        mixing a koji starter into said pulse crop,
        incubating said pulse crop while stirring, and
    hydrolyzing said koji preparation by adding a quantity of water approximately equal in weight to the weight of said koji preparation and keeping said koji preparation at 30°–65° C. for approximately 48 hours, whereby phytic acid contained in said pulse crop is removed and glycosidic saccharides contained in isoflavones are converted into aglycones.

7. A food product prepared from a pulse crop as a starting material, said product being prepared by the ordered steps of:
    preparing a koji preparation by the steps comprising:
        cooking said pulse crop,
        cooling said cooked pulse crop,
        adding water into said pulse crop,
        mixing a koji starter into said pulse crop,
        incubating said pulse crop while stirring, and
    hydrolyzing said koji preparation by adding water, whereby phytic acid contained in said pulse crop is removed and glycosidic saccharides contained in said pulse crop are hydrolyzed, thereby forming isoflavone compounds containing aglycones.

8. A food product prepared from a pulse crop as a starting material, said product being prepared by the ordered steps of:
    preparing a koji preparation by the steps comprising:
        cooking said pulse crop,
        cooling said cooked pulse crop,
        adding water into said pulse crop,
        mixing a koji starter into said pulse crop, and
        incubating said pulse crop while stirring;
    hydrolyzing said koji pulse crop by adding a quantity of water approximately equal in weight to the weight of said koji preparation and keeping said koji preparation at 30°–65° C. for approximately 48 hours, whereby phytic acid contained in said pulse crop is removed and glycosidic saccharides contained in isoflavones are converted into aglycones.

9. A food product prepared from a pulse crop as a starting material according to claim 8, further comprising a step of drying said koji pulse crop after said hydrolyzing step.

10. A food product prepared from a pulse crop as a starting material according to claim 9, further comprising a step of pulverizing said koji pulse crop after said drying step.

* * * * *